United States Patent [19]

Tsujii

[11] Patent Number: 4,729,100
[45] Date of Patent: Mar. 1, 1988

[54] CT SYSTEM WHICH CONVOLUTES PROJECTION DATA WITH A FREQUENCY VARYING FILTER FUNCTION

[75] Inventor: Osamu Tsujii, Tokyo, Japan

[73] Assignee: Kabushiki Kaisha Toshiba, Kawasaki, Japan

[21] Appl. No.: 767,860

[22] Filed: Aug. 21, 1985

[30] Foreign Application Priority Data

Aug. 28, 1984 [JP] Japan .............................. 59-178650
Dec. 28, 1984 [JP] Japan .............................. 59-276093
Dec. 28, 1984 [JP] Japan .............................. 59-276232

[51] Int. Cl.⁴ .................... G06F 15/42; A61B 6/03
[52] U.S. Cl. ............................................... 364/414
[58] Field of Search ...................................... 364/414

[56] References Cited

U.S. PATENT DOCUMENTS

| | | | |
|---|---|---|---|
| 4,326,252 | 4/1982 | Kohno et al. | 364/414 |
| 4,333,145 | 6/1982 | Heuscher et al. | 364/414 |
| 4,499,493 | 2/1985 | Nishimura | 364/414 X |
| 4,503,461 | 3/1985 | Nishimura | 364/414 X |
| 4,555,760 | 11/1985 | Op de Beek et al. | 364/414 |

Primary Examiner—Jerry Smith
Assistant Examiner—Clark A. Jablon
Attorney, Agent, or Firm—Oblon, Fisher, Spivak, McClelland & Maier

[57] ABSTRACT

X-rays are projected from different directions onto a specific slice of an object to be examined, and corresponding projection data is acquired. The projection data is divided into regions in accordance with the data characteristics. The regions are convoluted by corresponding filter functions having different frequency characteristics and are combined to obtain back-projection data, thereby reconstructing an image for the slice.

14 Claims, 31 Drawing Figures

F I G. 10
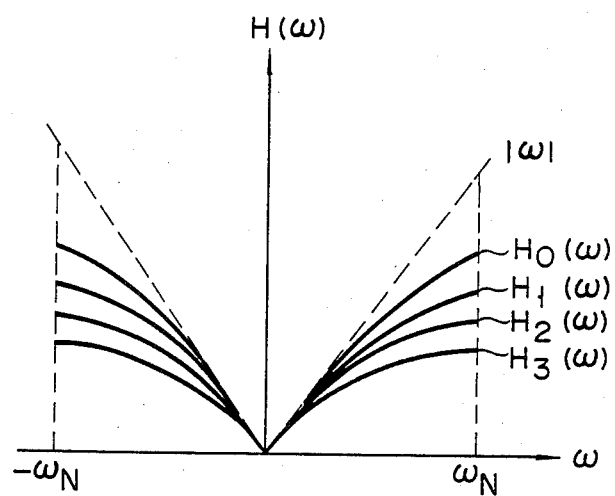
F I G. 11
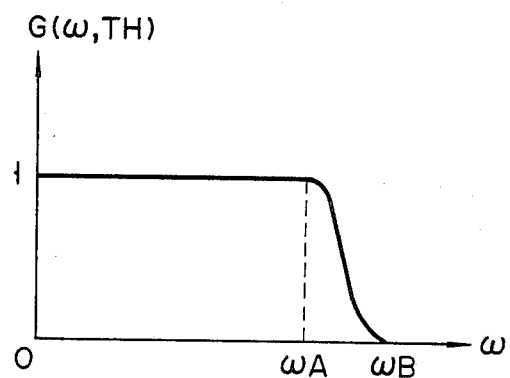

F I G. 19
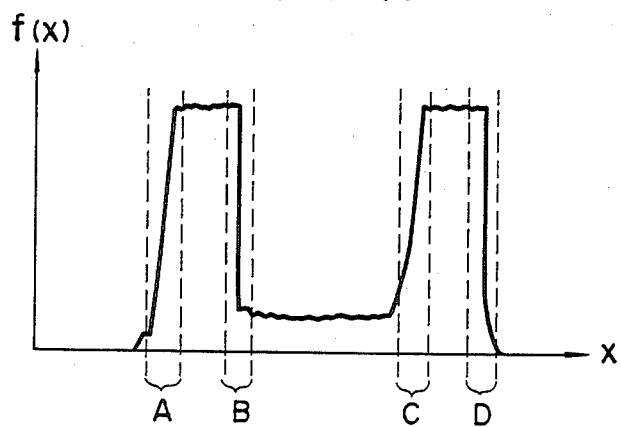
F I G. 20
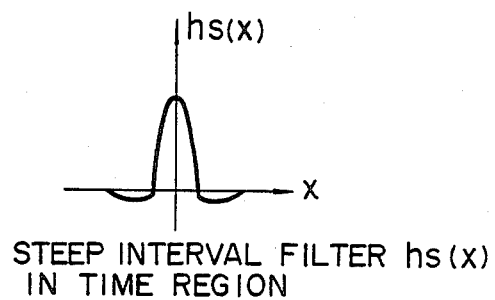
STEEP INTERVAL FILTER hs(x)
IN TIME REGION
F I G. 21
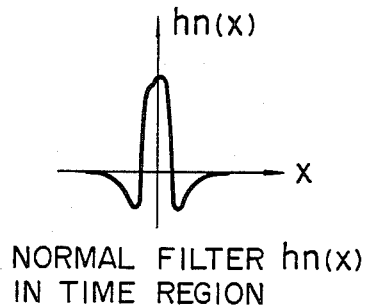
NORMAL FILTER hn(x)
IN TIME REGION

PROJECTION DATA AND
STEEP INTERVAL

IMAGE RECONSTRUCTION BY
FILTERS hs AND hn

F I G. 28
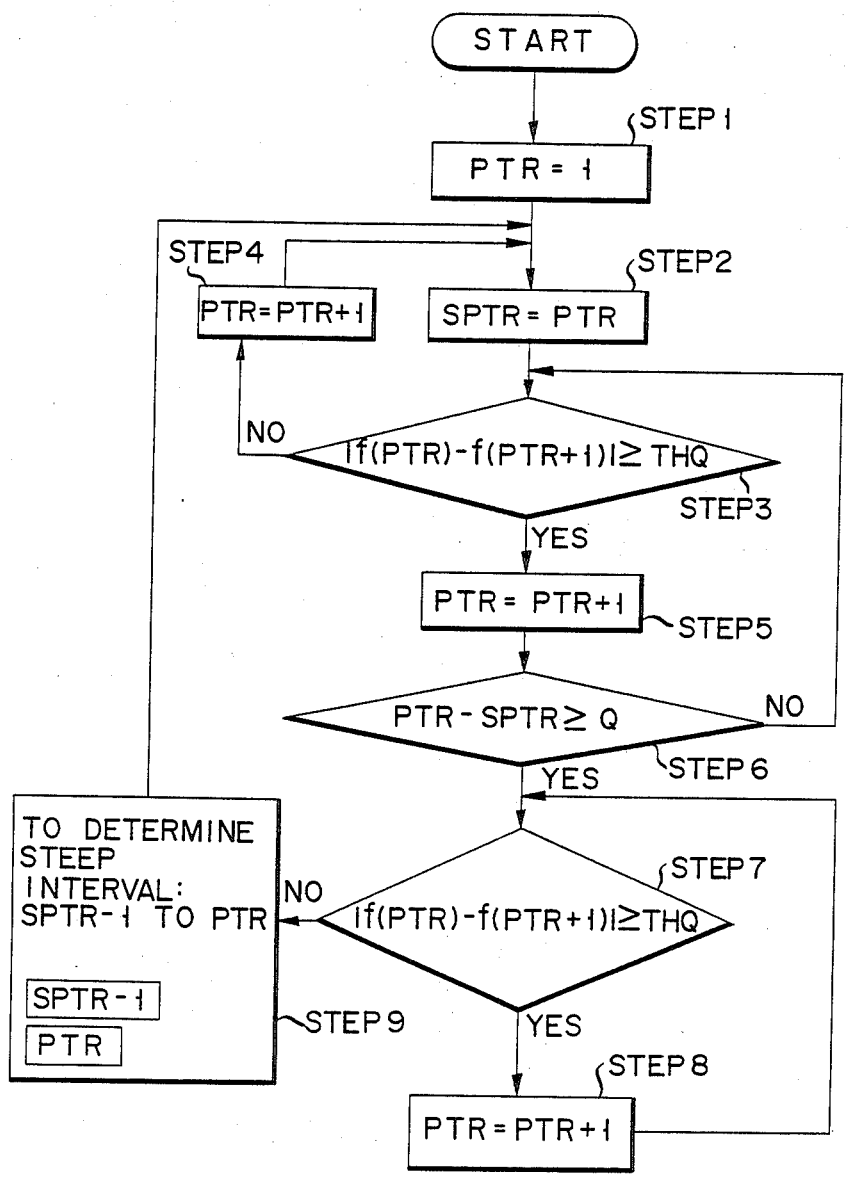

CT SYSTEM WHICH CONVOLUTES PROJECTION DATA WITH A FREQUENCY VARYING FILTER FUNCTION

BACKGROUND OF THE INVENTION

The present invention relates to a computerized tomographic apparatus for reconstructing a tomogram of an object of interest, thereby diagnosing the object.

Computerized tomography is known as a system for measuring the internal flaws, composition and structure of an object with high precision in a nondestructive manner.

Such computerized tomography uses a radiation source for radiating an X-ray as a flat fan beam expanding in a sector shape. The object to be measured is irradiated with the fan beam generated from the radiation source, and the fan beam is detected by a plurality of radiation sensors arrayed along the expansion direction of the fan beam. The radiation source is sequentially rotated in units of degrees through 180 degrees to 360 degrees while the radiation source is located opposite to the radiation sensors with the object at the center. X-ray absorption data from different directions of a slice of the object is acquired. The acquired data is reconstructed by a computer to form a tomogram. Therefore, image reconstruction can be performed with about 2,000 gradation levels at the respective positions in accordance with the composition, and the state of the slice can be examined in detail.

Computerized tomography of this type is called a 3rd generation system. In a 1st generation system, a radiation sensor is located opposite to a radiation source for radiating an X-ray as a pencil beam. The radiation source and sensor are traverse scanned along the slice of the object. The object or radiation source is rotated by a predetermined angle for every traverse scanning.

In a 2nd generation system, an X-ray as a fan beam with a narrow width and a plurality of radiation sensors are used. The radiation source and sensors are subjected to traverse and rotary scanning.

In a 4th generation system, a plurality of sensors are arranged around the object to be examined and are combined with a radiation source for radiating an X-ray as a fan beam with a large width. Only the radiation source is rotated.

Reconstruction process of the computerized tomography is typically classified into an analytic technique and an algebraic technique. Among these techniques, the analytic technique, especially filtered back projection is mainly used. According to filtered back projection, radiation intensity data is convoluted by using a filter function, and the resultant projection data is back projected to perform image reconstruction. Although such filtered back projection is very effective, noise is emphasized since the high-frequency component of the projection data is emphasized to improve resolution of the image. Assuming that noise included in the projection data is limited to quantum noise, an S/N ratio is decreased when a dose of radiation transmitted through the object is small. The image is thus degraded. This phenomenon also occurs when radiation is transmitted through a material with high absorbancy of radiation within a circular region of interest which is defined by the outermost edge of the X-ray during rotary scanning, and the dose of this radiation is very small.

When the dose of the source is small or the dose is locally decreased, the conventional filtered back projection method is not suitable for reconstructing the tomogram in accordance with the projection data.

Furthermore, the conventional filtered back projection method has a disadvantage in generation of artifacts as compared with approximation method. This disadvantage is typically observed when the number of projection data is small although an image to be reconstructed is complicated.

SUMMARY OF THE INVENTION

It is an object of the present invention to provide a computerized tomographic apparatus for reconstructing a slice of an object wherein quantum noise can be decreased and resolution is not degraded although filtered back projection is used and a material with a high radiation absorption coefficient is present, and at the same time, an artifact can be eliminated.

According to the present invention, there is provided a computerized tomographic apparatus for reconstructing a slice of an object wherein projection data can be convoluted by using a plurality of filter functions having different frequency responses.

According to the present invention, there is provided a computerized tomographic apparatus for reconstructing a slice of an object wherein an image of high quality can be obtained without degrading resolution, and the artifact can be eliminated.

BRIEF DESCRIPTION OF THE DRAWINGS

FIGS. 7 to 15 respectively show another embodiment of the present invention, in which FIG. 7 is a graph for explaining the basic principle of threshold setting, FIGS. 8 and 9 are graphs for explaining filter functions by utilizing the frequency characteristics, respectively, FIG. 10 is a graph for explaining filter functions used in the present invention, FIG. 11 is a graph showing a function $G(\omega, TH)$;

FIG. 12 is a flow chart for explaining the operation of the tomographic examination apparatus of this embodiment, and FIGS. 13 to 15 are respectively a flow chart and graphs for explaining the main part of the apparatus of this embodiment; and FIGS. 16 to 30 respectively show still another embodiment of the present invention, in which FIG. 16 is a block diagram of a tomographic examination apparatus of this embodiment, FIG. 17 is a detailed block diagram showing a fast reconstruction unit, FIG. 18 is a flow chart for explaining the processing procedures, FIG. 19 is a graph showing projection data, FIGS. 20 to 23 are respectively graphs for explaining filter processing by using two types of filter functions, FIGS. 24 to 26 are respectively graphs for explaining a steep interval extraction by using a differential, FIG. 27 is a functional block diagram for explaining the differential in a steep interval discriminator, FIG. 28 is a flow chart for explaining steep interval extraction by sequential discrimination, FIG. 29 is a functional block diagram for explaining sequential discrimination in the steep interval discriminator, FIG. 30 is a graph showing filter functions of the steep and normal intervals.

DETAILED DESCRIPTION OF THE PREFERRED EMBODIMENTS

The present invention will be described in detail with reference to preferred embodiments in conjunction with the accompanying drawings.

The present invention is exemplified by a 3rd generation CT scanner, but can be extended to CT scanners of other generations.

Figure 1:
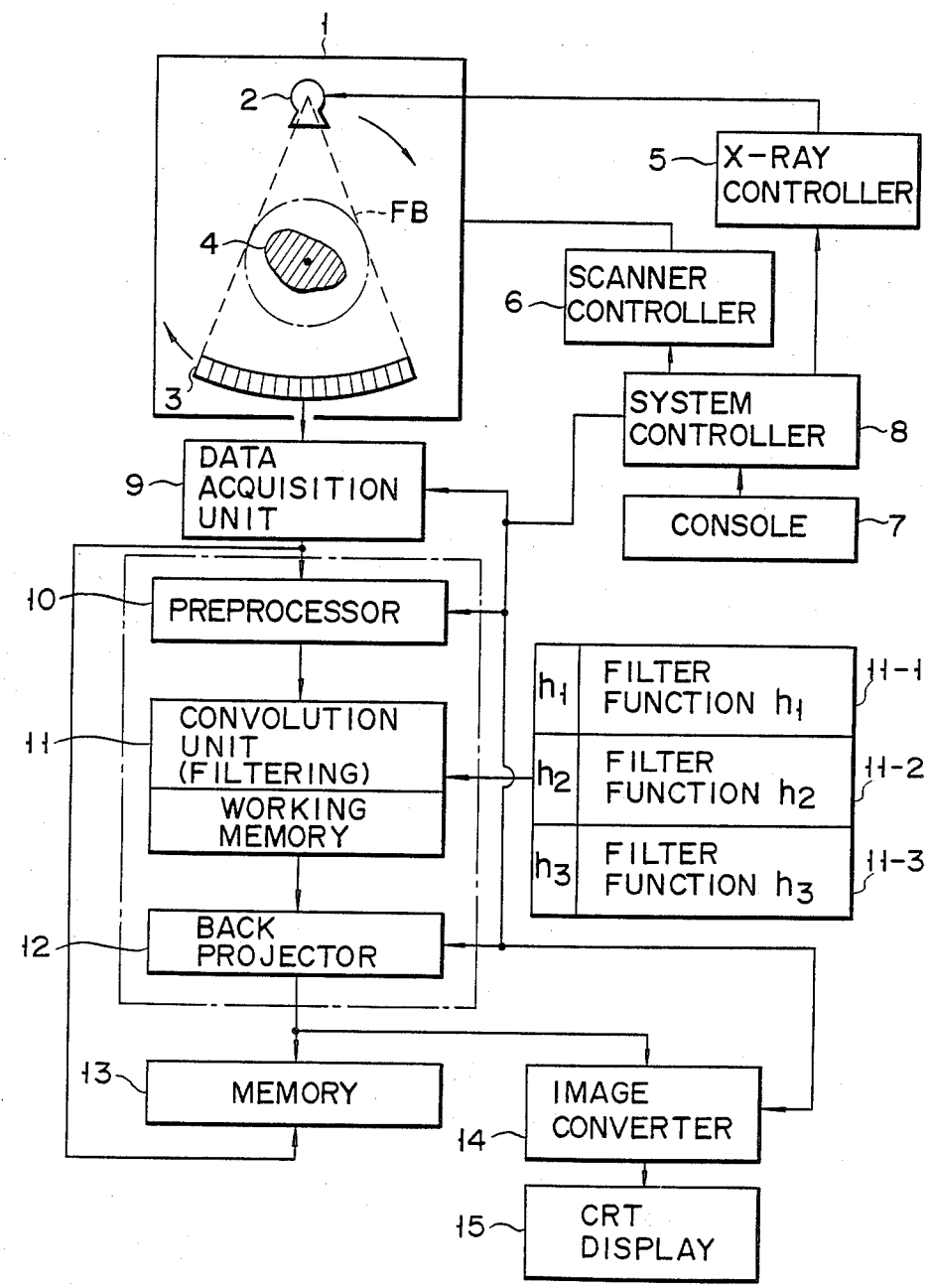
FIG. 1 is a block diagram of a computerized tomographic apparatus for reconstructing a slice of an object according to an embodiment of the present invention.

FIG. 1 is a block diagram showing the basic arrangement of a computerized tomographic apparatus for reconstructing a slice of an object. A scanner unit 1 comprises an X-ray source 2 for projecting an X-ray as a fan beam having a predetermined large width and a radiation sensor 3 which is located opposite to the source 2 and which has a plurality of sensor elements. The sensor elements are aligned along the X-ray beam expansion direction and have a spatial resolution, so that an X-ray intensity can be detected by the sensor 3. An object 4 to be examined is located along a path connecting the source 2 and the sensor 3. The sensor elements generate signals corresponding to the intensity of radiation beams on the path. The unit 1 also has a rotary table which is rotated by every predetermined angle with respect to the region of interest as the center while the source 2 and the sensor 3 oppose each other.

A tube current, a tube voltage and an X-ray dose of the source 2 are controlled by an X-ray controller 5. The rotary table of the unit 1 is controlled by a scanner controller 6 having a CPU operated in accordance with a prestored program.

Various operation commands and data entered by an operator at a console 7 to the system are supplied to the controllers 5 and 6 and to other respective components of the system through a system controller 8.

A detection signal from the sensor 3 is supplied to a data acquisition unit 9 and is A/D converted as X-ray absorption data to a preprocessor 10. The preprocessor 10 performs preprocessing operations such as log transform, gain correction and offset correction for each projection data acquired by the unit 9. The preprocessed data is supplied to a convolution unit 11. The unit 11 convolutes the preprocessed data and the convolution data is supplied to a back projector 12. The projector 12 back-projects the convoluted data in the projection direction to reconstruct a tomogram. The preprocessor 10, the convolution unit 11 and the back projector 12 constitute a reconstruction device. The back projection data obtained from the reconstruction device is stored in a memory 13. Data as a value (i.e., a CT value) corresponding to a level of radiation absorption falling within a desired range is read out from the memory 13. The CT value is generated as a monochrome image from an image converter 14. The monochrome image is displayed on a CRT display 15.

With this arrangement, the operator operates the console 7 to start the system. The system then performs tomographic examination. The system controller 8 controls the scanner controller 6, and the rotary table in the unit 1 is rotated by every predetermined angle, e.g., 0.6 degrees. The system controller 8 causes the X-ray controller 5 to supply a tube current and a tube voltage to the source 2 every time the unit 1 is rotated by the predetermined angle. A fan beam pulse FB is emitted from the source 2.

An object 4 is placed as the center of rotation on the rotary table between the source 2 and the sensor 3. The source 2 emits fan beams FB at different directions to a predetermined slice of the object 4. The intensities of the beam doses along the respective paths of the fan beams FB are detected by the corresponding sensor elements of the sensor 3 and are converted to electrical signals.

The electrical signals are acquired by the unit 9. The X-ray absorption data from each path for every projection is stored in the memory 13 is supplied to the unit 10. The unit 10 performs the log transform, the gain correction and the offset correction for every projection. The unit 11 convolutes the preprocessed data. The convoluted data is back-projected by the projector 12 to calculate a CT value for each pixel position. A tomogram is reconstructed by the resultant CT values. The reconstructed tomogram is stored in the memory 13. CT values in a desired range are converted by the converter 14 in accordance with the command from the console 7, and the converted image is displayed on the display 15 with a corresponding gradation level. As a result, the reconstructed image is displayed as a monochrome image.

Processing of the reconstruction device as the main unit in the tomographic examination apparatus will be described hereinafter. Reconstruction processing is classified into preprocessing, filter processing and back projection. Preprocessing includes correction operations (e.g., a reference correction and an offset correction) for the X-ray absorption data and log transform. Back projection aims at projecting the filtered data in the same direction as in data acquisition. Preprocessing and back projection are known techniques, and a detailed description thereof will be omitted.

Figure 2:
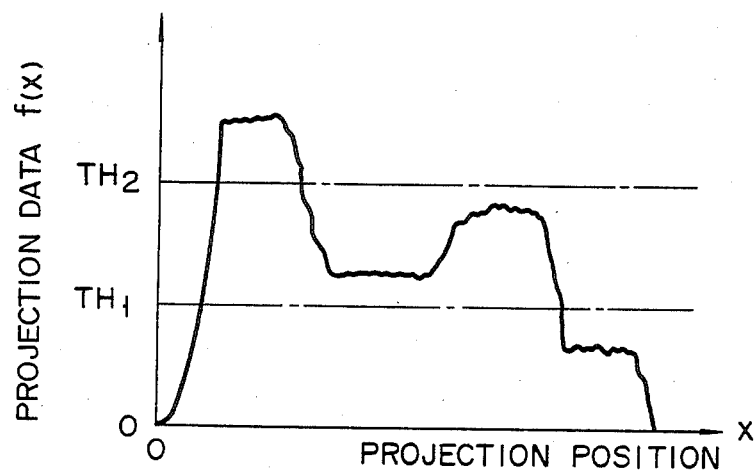
FIG. 2 is a graph for explaining the relationship between the projection data and its threshold values.

Filter processing in the unit 11 as the main part of the present invention will be described in detail. The preprocessed X-ray absorption data is called projection data $f(x)$. The projection data $f(x)$ is given in FIG. 2. The projection data $f(x)$ is represented by $f(x) = K \ln(PO/P(x))$ where $P(x)$ is the transmitted X-ray intensity detected by the sensor 3 and acquired by the unit 9, and PO is the number of photons in the X-ray generated from the source 2. The photon noise in the transmitted X-ray intensity $P(x)$ can be given by $\sqrt{P(x)}$. An S/N ratio of the transmitted X-ray intensity $P(x)$ is given as $P(x)/\sqrt{P(x)} = \sqrt{P(x)}$. When the transmitted X-ray intensity $P(x)$ is high, the acquired data has higher reliability. In other words, when the projection data $f(x)$ is small, the data reliability is good.

Figure 3:
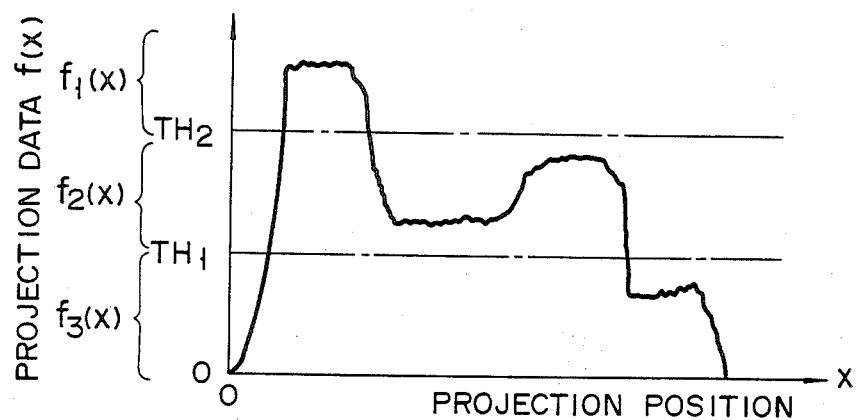
FIG. 3 is a graph for explaining the relationship between the projection data and the data regions discriminated by the threshold values.

Threshold values TH1 and TH2 are given in accordance with the degrees of reliability of the projection data $f(x)$. As shown in FIG. 3

| | |
|---|---|
| $0 \leq f(x) < TH_1$ | High Reliability Portion of Projection Data |
| $TH_1 \leq f(x) < TH_2$ | Medium Reliability Portion of Projection Data |
| $TH_2 \leq f(x)$ | Low Reliability Portion of Projection Data |

As shown in FIG. 3, the intensity f(x) is divided into $f_1(x)$, $f_2(x)$ and $f_3(x)$ with respect to the threshold values, and relation $f(x) = f_1(x) + f_2(x) + f_3(x)$ is satisfied. Intensities $f_1(x)$, $f_2(x)$ and $f_3(x)$ are given as follows:

$$f_1(x) = \begin{cases} 0 & (f(x) < TH_2) \\ f(x) - TH_2 & (f(x) \geq TH_2) \end{cases}$$

$$f_2(x) = \begin{cases} 0 & (f(x) < TH_1) \\ f(x) - TH_1 & (TH_1 \leq f(x) < TH_2) \\ TH_2 - TH_1 & (f(x) \geq TH_2) \end{cases}$$

$$f_3(x) = \begin{cases} f(x) & (f(x) < TH_1) \\ TH_1 & (TH_1 \leq f(x)) \end{cases}$$

From the evaluation of FIG. 3, f(x) is given such that:

| | |
|---|---|
| $f_1(x)$ | Low Reliability |
| $f_2(x)$ | Medium Reliability |
| $f_3(x)$ | High Reliability |

Figure 4:
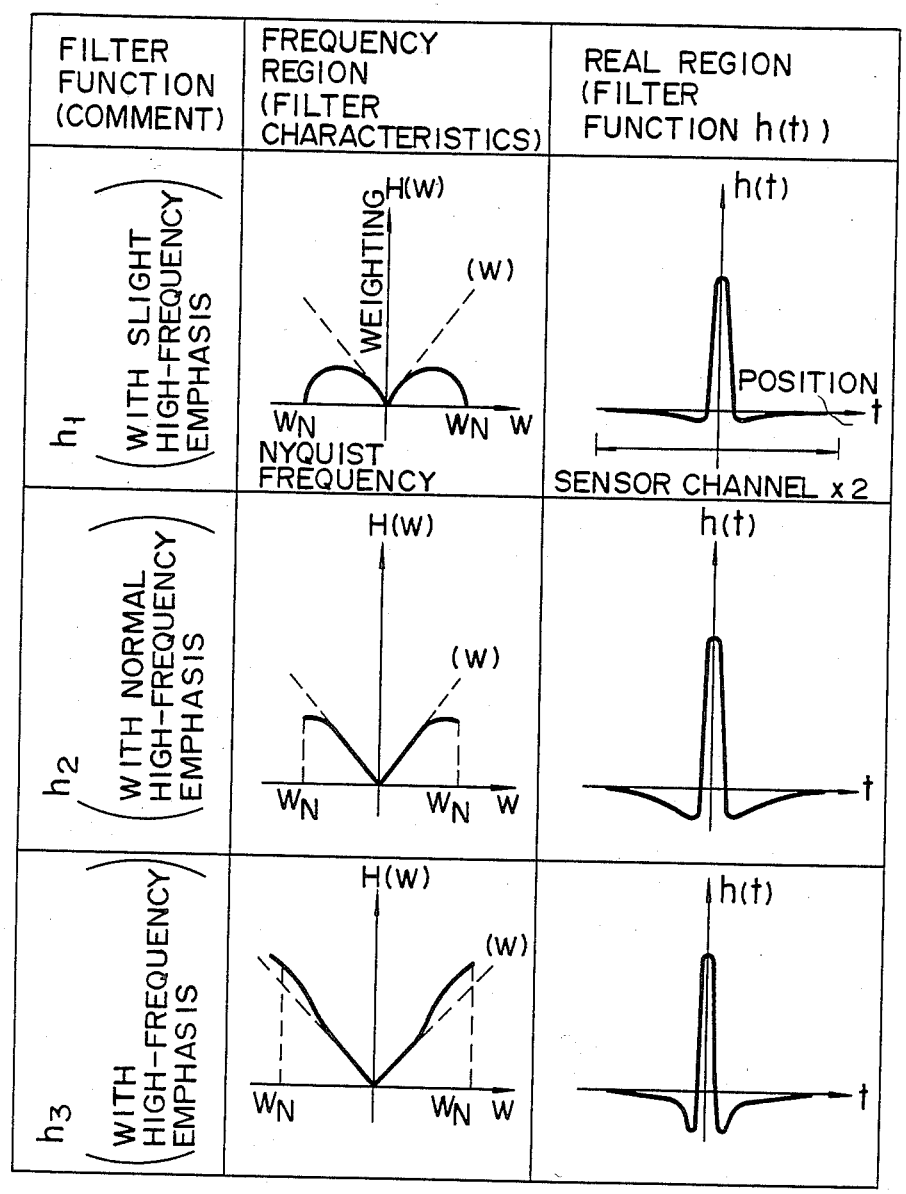
FIG. 4 is a table showing filter functions used in the present invention.

The high reliability data is free from image degradation even if its high-frequency component is emphasized. Different filter functions $h_1$, $h_2$ and $h_2$ are prepared in the unit 11, as shown in FIG. 4. A proper filter function corresponding to the data reliability is selected. The filter function $h_1$ slightly emphasizes the high-frequency component, the filter function $h_2$ normally emphasizes the high-frequency component, and the filter function $h_3$ emphasizes the high-frequency component, as shown in FIG. 4. The unit 11 changes the high-frequency emphasis degree in accordance with the proper filter function h corresponding to the reliability degree of the data to be convoluted.

Figure 5:
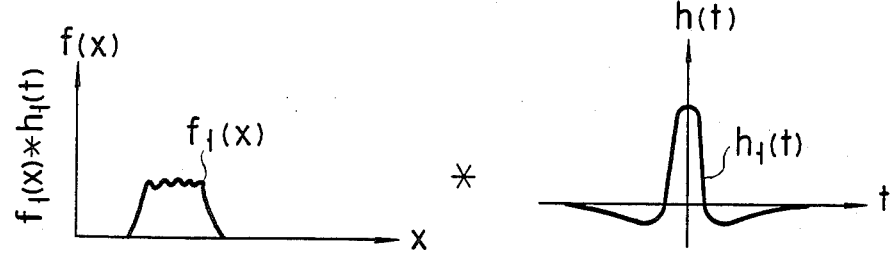
FIG. 5 shows graphs for explaining divided convolution method according to the present invention.
Figure 5:
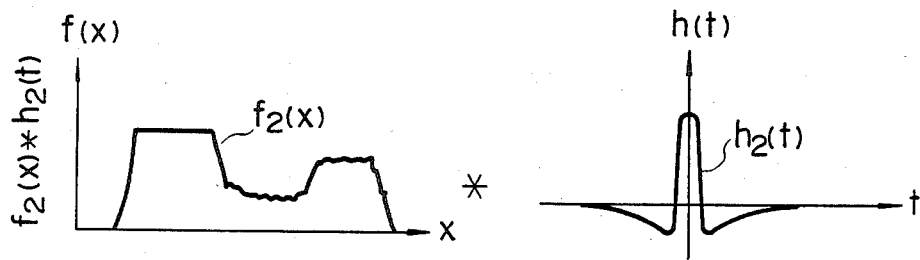
Figure 5:
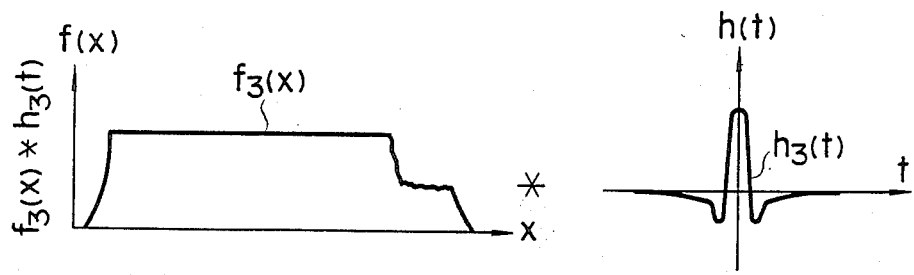

Referring to FIG. 4, H(ω) is a spectrum and WN is the Nyquist frequency. The convolution technique will be described with reference to FIG. 5. Since convolution is a linear operation, the projection data f(x) can be divided into $f_1$, $f_2$ and $f_3$ in accordance with the levels thereof.

The projection data f(x) shown in FIG. 3 is given as f and is divided into units $f_1$, $f_2$ and $f_3$ by comparing the levels of the data with the threshold values $TH_1$ and $TH_2$ thereof. Under the above assumption, $f = f_1 + f_2 + f_3$ is established, and $f_1$, $f_2$ and $f_3$ correspond to $f_1(x)$, $f_2(x)$ and $f_3(x)$ of FIG. 5, respectively. The filter functions $h_1$, $h_2$ and $h_3$ corresponding to the reliability degrees of the projection data $f_1(x)$, $f_2(x)$ and $f_3(x)$ are selected therefor, and convolution is performed. The projection data components $f_1(x)$, $f_2(x)$ and $f_3(x)$ are added to obtain f*h = $(f_1(x) + f_2(x) + f_3(x)) *h = f_1(x)*h_1 + f_2(x)*h_2 + f_3(x)*h_3$ where * is the convolution.

The filter functions $h_1$, $h_2$ and $h_3$ are selected in accordance with the reliability degrees of the projection data components, and convolution is performed by using the selected filter function. The convoluted projection data components are added to change the high-frequency emphasis degrees for the respective data regions in accordance with the reliability degrees. When data is free from influence of the high-frequency emphasis, the high-frequency component of this data is emphasized. The resultant data f*h is supplied to the projector 12 and is back projected to obtain a reconstructed image having an improved resolution without degrading the image quality.

The threshold values $TH_1$ and $TH_2$ for dividing the projection data f(x) into the components $f_1$, $f_2$ and $f_3$ will be described. In order to simply set the threshold values $TH_1$ $TH_2$, the dynamic range of the projection data f(x) can be equally divided into three regions. For example, when projection data f(x) has a dynamic range of 32767 to −32768, $$TH_2 = 10923$$

$$TH_1 = -10923$$

Filtering is performed by the filter function $h_1$ in the following range:

$$10923 < f(x) < +32767$$

Filtering is performed by the filter function $h_2$ in the following range:

$$-10923 < f(x) < 10923$$

Filtering is performed by the filter function $h_3$ in the following range:

$$-32768 < f(x) < -10923$$

In practice, however, the three regions must be obtained in a range higher than the standard value "0" since a material serving as a standard material is normally selected with a high S/N ratio. Therefore, the S/N ratio can be high when the divided regions have values exceeding the standard value "0".

In an industrial product containing a high absorption material, e.g., a metal as a major constituent, the threshold values $TH_1$ and $TH_2$ are set to be 10000 and 1000 in accordance with the composition. In this case, the filter function $h_1$ is used for $10000 \leq f(x) \leq 32767$; the filter function $h_2$ is used for $1000 \leq f(x) < 10000$; and the filter function $h_3$ is used for $-32768 \leq f(x) < 1000$.

Unlike in the conventional filtered back projection which fails to decrease the noise component without degrading resolution, the technique of this embodiment can decrease the noise component without degrading resolution. The filter processing of this embodiment can be achieved by a simple, inexpensive arrangement by adding a simple logic and a memory to the conventional reconstruction device. When image reconstruction is perforemd by using projection data representing a large shortage of the dose, a component with a relatively high dose is especially high-frequency emphasized, and a portion with a high noise component is subjected to smoothing, thereby obtaining a high-quality image with low noise as compared with the conventional image.

In the above embodiment, the projection data f(x) is divided by additional division. However, proportional additional division may be used in place of additional division. In this case, in the same manner as in FIG. 3, when $f(x) = f1(x) + f2(x) + f3(x)$ is given:

$$f_1(x) = \begin{cases} 0 & (f(x) < TH_2) \\ f(x)/3 & (f(x) \geq TH_2) \end{cases}$$

$$f_2(x) = \begin{cases} 0 & (f(x) < TH_1) \\ f(x)/2 & (TH_1 \leq f(x) \leq TH_2) \\ f(x)/3 & (f(x) \geq TH_2) \end{cases}$$

$$f_3(x) = \begin{cases} f(x) & (f(x) < TH_1) \\ f(x)/2 & (Th_1 \leq f(x) < TH_2) \\ f(x)/3 & (f(x) \geq TH_2) \end{cases}$$

Although the resolution obtained by proportional additional division is lower than that of additional division, the noise component can be decreased.

Figure 6:
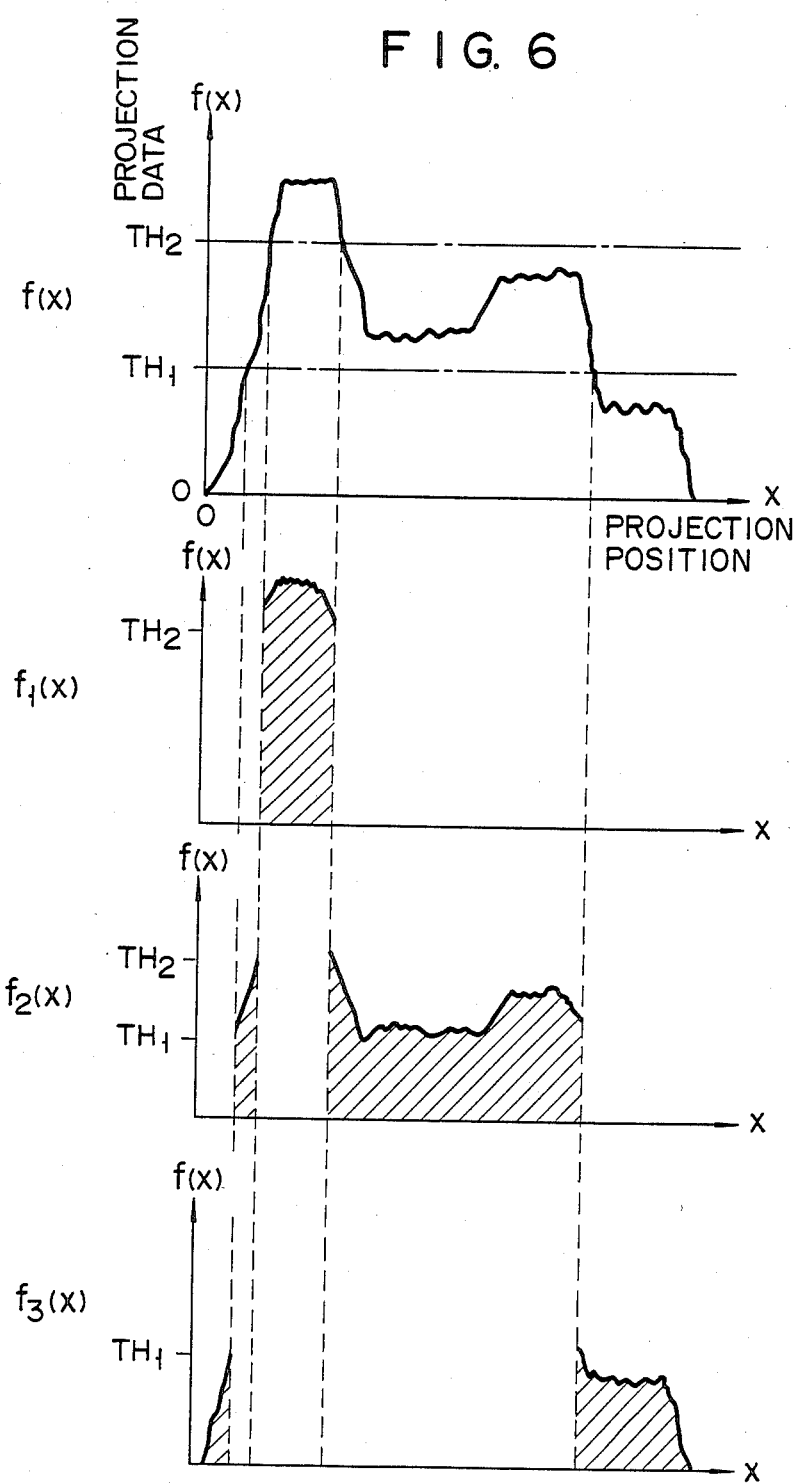
FIG. 6 shows graphs for explaining a modification of the present invention in divide method of projection data.

As shown in FIG. 6, the projection data f(x) may be given as $f(x) = f_1(x) + f_2(x) + f_3(x)$ and may be divided into $f_1(x)$, $f_2(x)$ and $f_3(x)$ by using the threshold values $TH_1$ and $TH_2$. In the method of FIG. 6, for each of the level regions (obtained by a proportionate distribution system), convolution is performe in accordance with the corresponding filter functions, and addition is thereafter performed. However, in the method of FIG. 6, respective outputs from the sensor elements are discriminated to determine if they exceed the threshold values or not. The method of FIG. 6 is level correspondence division. Only the filter function $h_1$ is used to convolute the projection data $f_1(x)$ having a level higher than the threshold value $TH_2$. Only the filter function $h_2$ is used to convolute the projection data having a level higher than the threshold value $TH_1$ and lower than the threshold value $TH_2$. Only the filter function $h_3$ is used to convolute the projection data $f_3(x)$ having a level lower than the threshold value $TH_1$. The above division is very effective for reliability of the projection data.

In each embodiment, the projection data is divided into three components. However, the number of divided components can be two, four or more. In this case, the filter functions must be provided for the respective division regions, i.e., divided components. When the number of division regions is increased, a convolution time is prolonged.

In the above embodiment, filtering is performed for the real region, but can be performed for the frequency region.

Fourier transform is a linear transform. When F is given as a Fourier transform and relation $F(f(x))$ $F(\nu)$ is established, the following equation is established:

$$f(\nu) \triangleq F(f(x)) = F(f_1(x) + f_2(x) + f_3(x))$$
$$= F(f_1(x)) + F(f_2(x)) + F(f_3(x))$$
$$= F_1(\nu) + F_2(\nu) + F_3(\nu)$$

The frequency of the filtered projection data is given as:

$$F(\nu) \times H(\nu) = F_1(\nu) \times H_1(\nu) + F_2(\nu) \times H_2(\nu) + F_3(\nu) \times H_3(\nu)$$

for $F(h(t))$ $H(\nu)$

Alternatively, the threshold values may be given in consideration of level distribution of the projection data of the present invention so as to derive filter functions of the frequency responses corresponding to respective intervals. This operation must be performed by a reconstruction device in the following manner.

The reconstruction processing is classified into preprocessing, filter processing and back projection which are implemented by the preprocessor 10, the convolution unit 11 and the back projector 12 of FIG. 1. The preprocessor 10 performs various corrections (e.g., reference correction, offset correction and standard correction of the X-ray absorption data) and log transform. The back projector 12 projects the filtered data in a data acquisition direction.

The filter processing in the unit 11 can be classified into the following methods.

(A-1) First, individual projection data are respectively filtered in accordance with the division. The projection data f(x) for each projection is divided into a predetermined number of regions in accordance with the level distribution thereof. A filter function corresponding to each region is selected or calculated, and the corresponding projection data is filtered.

(A-2) Second, by analyzing projection data for each or specific projection, a standard filter function is obtained and is used to filter data of all projections or a specific projection. An occurrence distribution of the data values is calculated in accordance with the respective distributions of the projection data f(x) of all projections or the specific projection. The data values are divided into a predetermined number of regions by accordance with the occurrence distribution, thereby calculating the filter functions corresponding to the respective regions. The projection data f(x) of all projections or the specific projection is filtered in accordance with the respective filter functions.

The division of projection data or regions of the occurrence distribution is selectively performed in accordance with the following two techniques.

(B-1) First, maximum and minimum values of the protection data or the like are calculated, and regions above the standard level are further divided into a predetermined number of regions.

(B-2) Second, a change in distribution of the projection data or the like is checked, and the projection data is divided in accordance with this change.

Still another two techniques can be selectively used when filter functions respectively corresponding to the regions are derived.

(C-1) First, each filter function is calculated in accordance with a threshold value between the two adjacent regions or a value of interest (i.e., a middle value) within the region.

(C-21) Second, an empirically derived filter function is selected in accordance with the threshold value or the value of interest within the region.

The above techniques for dividing the projection data into the predetermined regions and selection of the filter functions for each region can be selectively used in accordance with the state of the image.

The following filtering is performed by a device of FIGS. 7 to 15 in accordance with the first filtering technique (A-1), the first technique for division of the projection data into the predetermined regions and selection of filter functions (B-1).

In this embodiment, the distribution of the projection data f(x) as the preprocessed X-ray absorption data is checked to obtain maximum and minimum values. A range between the maximum and minimum values is calculated, and threshold values $TH_1$ and $TH_2$ are calculated to equally divide the range into three regions.

Filter functions corresponding to the threshold values are calculated, and the respective projection data components are filtered by the corresponding filter functions.

When general computerized tomography is used, a peripheral region of an object to be examined is air which is the substance having the smallest X-ray absorption. The minimum projection data (to be referred to as a MIN hereinafter) having the smallest X-ray absorption coefficient is always detected around the object. The resultant data values are identical when the computerized tomography is always calibrated under predetermined conditions.

Figure 7:
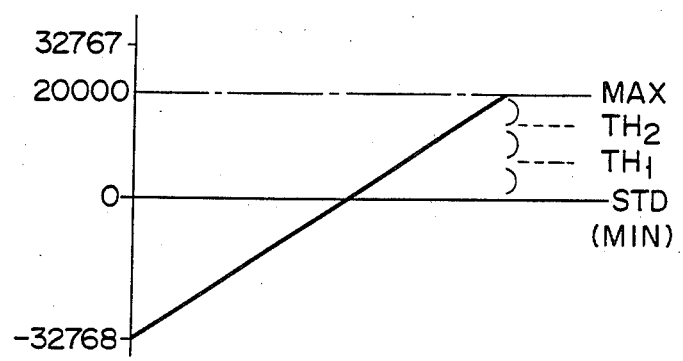

When maximum projection data (to be referred to as a MAX hereinafter) having the largest X-ray absorption is obtained, the threshold values $TH_1$ and $TH_2$ can be derived in accordance with a difference between the MIN and the MAX, as shown in FIG. 7. FIG. 7 shows a distribution range of the projection data values. The level range of the system is given as 32767 to −32768, and the projection data values fall within the range of −32768 to 20000 in FIG. 7. The MIN (i.e., −32768) represents air having the smallest X-ray absorption coefficient. The MAX is presumed to represent metals such as lead, iron, copper and tungsten contained in the object to be measured.

The data value "0" corresponds to a middle measurement value within the possible X-ray intensity measurement range. More specifically, the data "0" corresponds to the projection data representing water.

In order to calibrate in computerized tomography, a phantom of a water-containing cylindrical vessel of acrylic resin or the like is used as a standard calibration object. Calibration can be performed while the reconstructed image of the water phantom is being observed.

The water phantom aims at deriving the standard data. After calibration, when a material having a smaller X-ray absorption than that of water is measured by using a filter function whose frequency characteristics extend up to a high-frequency region, low noise is typically detected since such a material has a sufficiently higher signal level than that of the noise level.

The low noise level, that is, the level of water is given as the STD. When the threshold values $TH_1$ and $TH_2$ are given to equally divide the data distribution range between the STD and the MAX into three regions, the threshold calculations can be simplified. In this case, the frequency response of the filter functions used for deriving a reconstructed image of best quality can match with the distribution region of the data values.

The range between the MAX and the STD is divided into three regions, and filter functions hi(s) (i=0, 1, 2, 3) are assigned to the respective regions.

More specifically, the following filter functions are assigned to the projection data satisfying the corresponding conditions as follows:

$h_0(x)$ for $f(x) \leq STD$
$h_1(x)$ for $STD < f(x) \leq TH_1$
$h_2(x)$ for $TH_1 < f(x) \leq TH_2$
$h_3(x)$ for $TH_2 < f(x)$ Among the filter functions $h_0(x)$ to $h_3(x)$, the function $h_0(x)$ has best high-frequency response, and the functions $h_1(x)$, $h_2(x)$ and $h_3(x)$ have the next best high-frequency response in the order named.

As an exceptional case, all the projection data satisfy the condition MAX≦STD. In this case, since all the projection data used for image reconstruction have a level lower than the STD, a low noise reconstructed image can be obtained even if a filter function having high frequency characteristics is used. Division filtering using the threshold values need not be performed. In this case, all the data can be convoluted by using the filter function $h_0(x)$.

The division technique of the range between the STD and the MAX of the projectio data having a normal data value distribution excluding the exceptional case described above will be described hereinafter.

The quantum noise having a normal distribution depends on a square root of the number of transmitted photons. The projection data $f(x)$ is a log value $f(x)=K\ln(P0/P(x))$ of the transmitted X-ray intensity $P(x)$. More strictly, the transmitted X-ray intensity data are given as follows:

$$\left.\begin{array}{ll} P_{STD} & \text{for } f(x) = STD \\ P_{TH1} & \text{for } f(x) = TH_1 \\ P_{TH2} & \text{for } f(x) = TH_2 \\ P_{MAX} & \text{for } f(x) = MAX \end{array}\right\} \quad (1)$$

wherein the transmitted X-ray intensity data satisfy condition $P_{STD} > P_{TH1} > P_{TH2} > P_{MAX}$ and K is the contant.

When square roots of the transmitted X-ray intensity data are derived in equations (1), threshold values $TH_1$ and $TH_2$ for equally dividing the difference between the $P_{STD}$ and the $P_{MAX}$ are given by equations (2) and (3) since an S/N ratio of the $P_{STD}$ is higher than that of the $P_{MAX}$:

$$\sqrt{P_{TH1}} = \sqrt{P_{STD}} + (\sqrt{P_{MAX}} - \sqrt{P_{STD}})/3 \quad (2)$$

$$\sqrt{P_{TH2}} = \sqrt{P_{MAX}} - (\sqrt{P_{MAX}} - \sqrt{P_{STD}})/3 \quad (3)$$

Therefore, equation $f(x)=K\ln(P0/P(x))$ provides:

$$TH_1 = K\ln(9 \times P_0)/(\sqrt{P_{MAX}} + 2\sqrt{P_{STD}})^2 \quad (4)$$

$$TH_2 = K\ln(9 \times P_0)/(2\sqrt{P_{MAX}} + \sqrt{P_{STD}})^2 \quad (5)$$

Equations (4) and (5) make it possible to set threshold values for equally dividing the projection data with respect to its S/N ratio. According to another division technique, the projection data $f(x)$ is divided into three regions to derive simple equations (6) and (7) as follows:

$TH_1 = (MAX - STD)/3 + STD$ ...(6)

$TH_2 = MAX - (MAX - STD)/3$ ...(7)

As is apparent from equations (6) and (7), in this case, the range between the STD and the MAX is divided into three equal values, and the resultant value is added to the STD to derive the threshold value $TH_1$. The resultant value is subtracted from the MAX to obtain the threshold value $TH_2$. One of the above threshold setting techniques can be properly selected.

A filter function setting technique, i.e., selection of filter functions corresponding to the respective regions (the threshold values) will be described hereinafter. This technique involves empirical factors. It is difficult to quantitatively systemize filter function setting since proper images vary depending on shape/dimension data or composition distribution data in accordance with the type of material.

For this reason, the high-frequency response are designed to be smoothed from the filter function $h_0(x)$ to the filter function $h_3(x)$, and the filter function is qualitatively defined.

The relationship between the threshold value TH and the filter function $h(x)$ will be described hereinafter.

Figure 8:
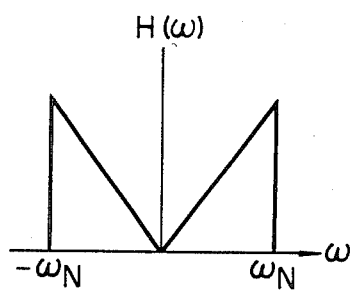
Figure 9:
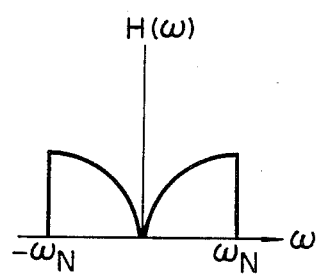

The filter function $h(x)$ is expressed by the frequency region, as shown in FIGS. 8 and 9.

FIG. 8 shows a function proposed by Ramachandran. In this function, an absolute value $|\omega|$ is intercepted by a Nyquist frequency $\omega N$. FIG. 9 shows a Sheppu-Logan's function. The high-frequency range extends in the Ramachandran function as compared with that of Sheppu-Logan's function. The Ramachandran function can provide a clear image, but the image is easily influenced by noise.

The filter functions can be distinguished from each other in accordance with the frequency response. For example, the $H(\omega)$ for $\omega N$ in the Ramachandran's function of FIG. 8 can constitute a filter for high-frequency emphasis as compared with that constituted by the Sheppu-Logan's function of FIG. 9.

The relationship between the filter frequency response and the threshold values will be described hereinafter. This relationship qualitatively provides higher frequency emphasis from the filter function $H_3$ to the filter function $H_0$. It should be noted that the filter function $H(\omega)$ is the function of the threshold value TH. That is, $$H(\omega) = H_0(\omega) \times G(\omega, TH) \quad \ldots (8)$$

where $H_0(\omega)$ is the standard characteristic and $G(\omega, TH)$ is the function between an angular frequency $\omega$ and the threshold value TH.

In the above embodiment, the standard response filter function $H_0(\omega)$ is derived from the Sheppu-Logan's function as follows:

$$H_0(\omega) = |(2\omega N/\pi)\sin(\pi\omega/2\omega N)| \{\sin(\pi\omega/2\omega N)/(\pi\omega/2\omega N)\}^2 \quad (9)$$

where $\omega N$ is the Nyquist frequency. The function $G(\omega, TH)$ is given by equation (10):

$$G(\omega, TH) = \begin{cases} 1 & \text{for } (0 \leq \omega < \omega A) \\ [1 + \cos\pi\{(\omega - \omega A) / (\omega B - \omega A)\}]/2 & \text{for } \omega \geq \omega A \end{cases} \quad (10)$$

FIG. 11 is a graph showing the function of equation (10). $\omega_A$ and $\omega_B$ in equation (10) are given:

$$\omega A = \omega N \cdot \{1 - (TH - STD)/K\}$$

$$\omega B = \omega N$$

where K is the constant.

The more the threshold value TH is increased, the smaller $\omega_A$ than $\omega N$. The high-frequency gain is decreased to prevent high-frequency emphasis. The threshold values $TH_1$ and $TH_2$ are determined in the manner described above, and the projection data is divided into four regions. The optimal filter functions are calculated in accordance with the S/N ratios of the respective regions. By using the filter function, the projection data of each projection direction is filtered. The filtered data is supplied to the back-projector 12 which then back-projects the data in a direction corresponding to the projection direction, thereby reconstructing the image.

Figure 12:
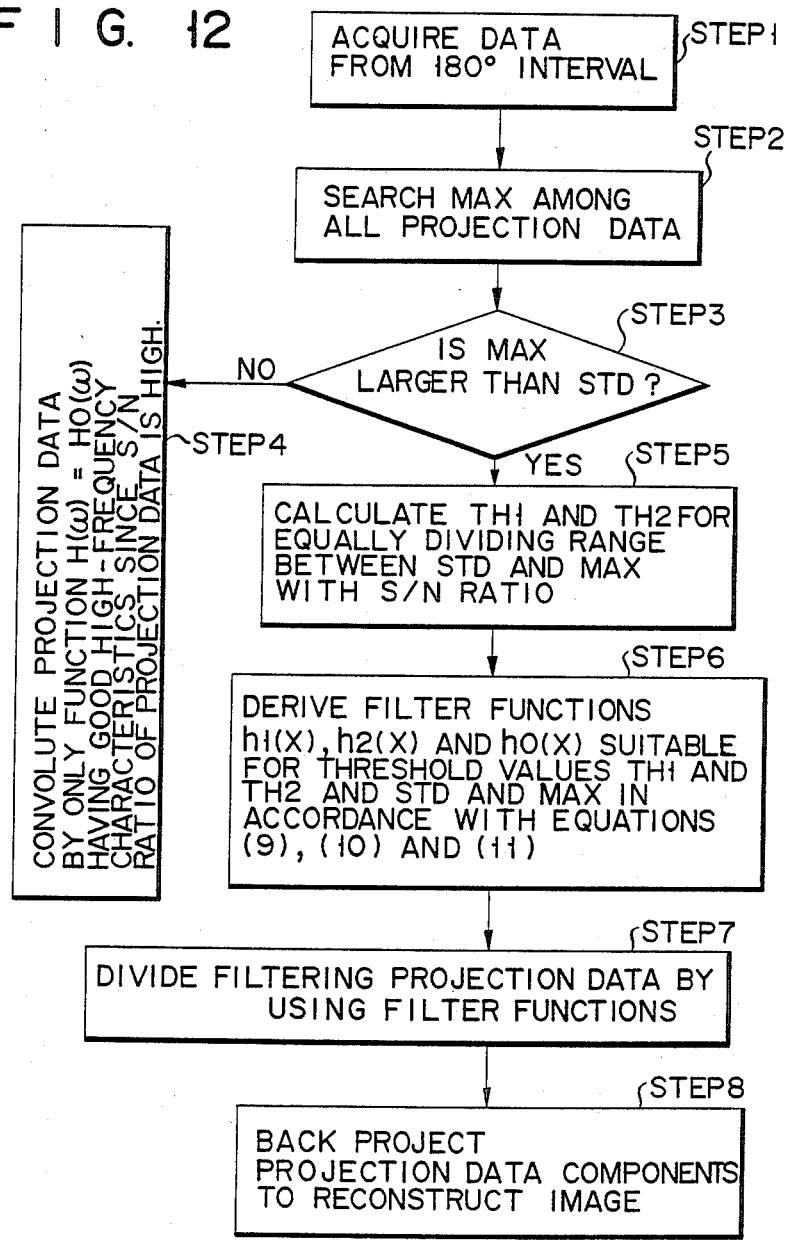

The processing procedures in the unit 11 and the projector 12 will be described with reference to a flow chart of FIG. 12.

In step 1, X-rays are projected from different directions falling within the range of 0 degrees to 180 degrees onto a slice of the object to obtain corresponding transmission data. The transmission data is preprocessed. When data acquisition is performed by using the fan beam, the fan beam is converted to parallel beams of the respective projection directions, so that projection data along all directions can be obtained by the corresponding parallel beams.

In step 2, the unit 11 is operated. A maxmimum value (i.e., the MAX of X-ray absorption) of each of the parallel projection data for all projection directions is searched.

Step 3 is executed to determined whether or not the MAX searched in step 2 is larger than the standard reliablity level STD. If NO in step 3, the projection data has a high S/N ratio and need not be subjected to division filtering. In step 4, the projection data is convoluted by using only the filter function $H0(\omega)$ having high-frequency emphasis characteristics. The respective projection data are back-projected by the back-projector 12 to reconstruct the image.

If YES in step 3, however, a range between the STD and the MAX is checked to obtain the threshold values $TH_1$ and $TH_2$ for equally dividing the range into three regions in step 5.

In step 6, filter functions $h_1(x)$, $h_2(x)$, $h_3(x)$ corresponding to the threshold values $TH_1$ and $TH_2$, the STD and the MAX are derived.

The projection data is divided into the regions, and the filter functions corresponding to the respective regions are used to convolute the projection data components of the respective projection directions, thereby obtaining projection data of the respective projection directions in step 7.

The projection data obtained in step 7 are back projected by the projector 12 in step 8 to reconstruct the image.

According to this embodiment, the maximum values of the projection data for one slice along the respective projection directions are obtained. The range between each maximum value and the standard value guaranteeing reliablity is calculated in accordance with the corresponding S/N ratio. The threshold values for equally dividing the range into three regions are calculated, and the filter functions for the respective divided regions are derived. The optimal filter functions having high-frequency response in accordance with the reliability degrees of the respective regions are calculated. For the region which can guarantee reliability, the filter function having high-frequency emphasis characteristics is used to filter the corresponding projection data. As a result, the image is reconstructed in accordance with the filtered projection data.

The data can be divided into the regions in accordance with the range irrespective of the regions including the standard reliable data to the data having a large X-ray absorption in accordance with the maximum value data of the acquired projection data. By using the filter functions derived in accordance with the reliability degrees of the S/N ratios of the respective regions, the maximum high-frequency emphasis can be performed in accordance with the maximum values of the X-ray absorption data. Therefore, the resolutions of the respective projection data can be maximized in accordance with the reliability degrees thereof.

An apparatus using the second filtering technique, the second projection data division technique for the operations of the unit 11 and the second filter function selection technique, as described above, will be described with reference to FIGS. 13 to 15.

In this embodiment, an occurrence distribution measuring unit 16 calculates an occurrence distribution of the projection data f(x), that is, a discrete signal (FIG. 14) quantized in correspondence with each sensor element of the radiation sensor. The occurrence distribution measurement can be performed for the projection data of all or specific projection directions. The resultant occurrence distribution data (FIG. 15) is supplied to an occurrence distribution dividing unit 17 which calculates a change (dA(f(x))/df(x)). The projection data values satisfying a condition that the change exceeds a predetermined value are calculated as threshold values. A filter function generator 18 has different filter functions obtained empirically or calculated by equation (8). These different filter functions are stored in a memory in the generator 18. The generator 18 selects a filter function solely determined by the threshold value. The projection data f(x) is sequentially filtered in accordance with the filter function. The filtered projection data are sequentially supplied to a back projector.

Figure 13:
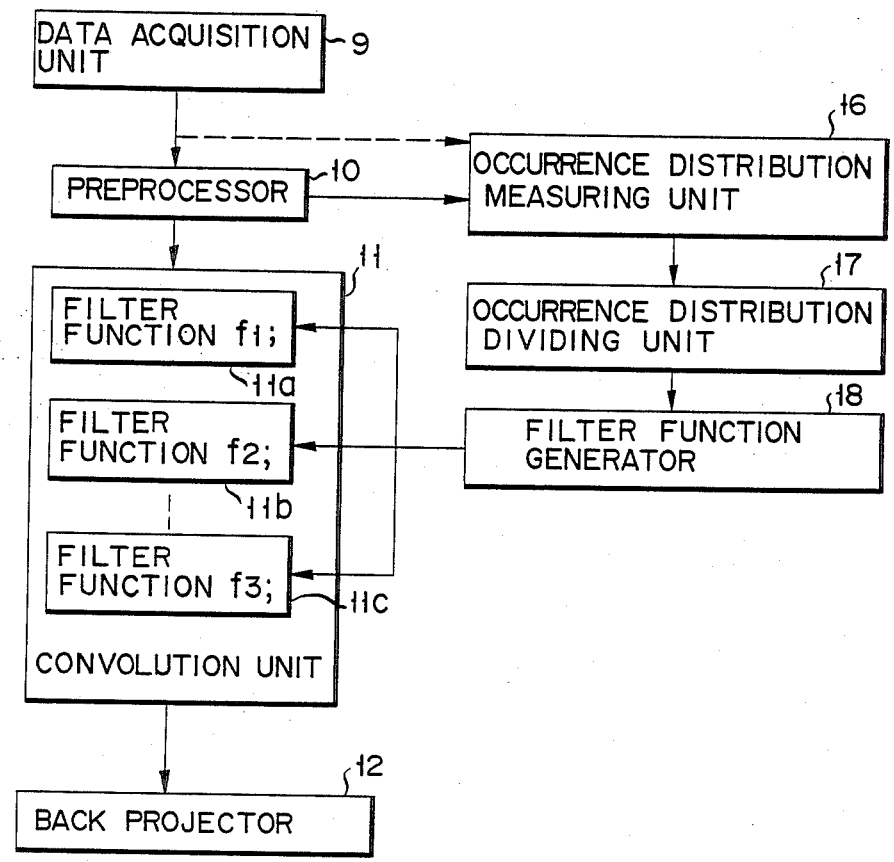
Figure 14:
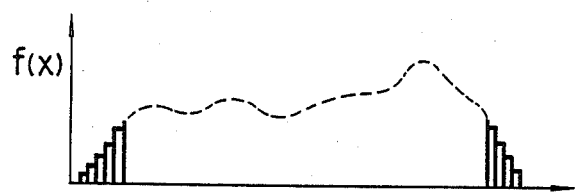
Figure 15:
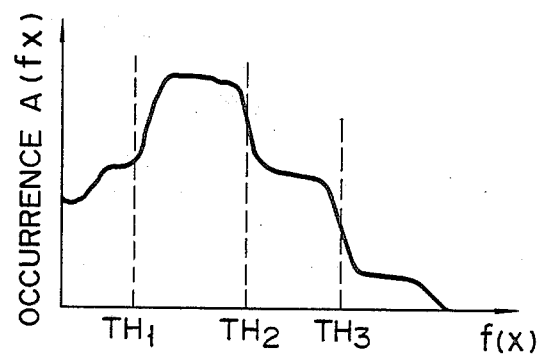

In the main part shown in FIG. 13, the projection data f(x) is divided into predetermined regions in accordance with the occurrence distribution, and corresponding filter functions are calculated to filter the corresponding projection data. Desired filtering, region division and filter function selection techniques can be used to achieve the same effect as in the previous embodiment.

In the above embodiment, the projection data is divided into three regions. However, the number of divided regions is not limited to three, but can be extended two, four or more.

Filtering is performed in the real region, but can be performed in the frequency region.

The above-mentioned threshold values can be modified in accordance with the actual standard material data and the composition of the object to be measured.

The filtered-back projection has a disadvantage in easy occurrence of an artifact as compared with approximation method. This can be typically observed when the number of projections is small as compared with complexity of an image. In this case, the projection data is divided in accordance with the degree of steepness of a change in projection data. The projection data during the steep interval is convoluted and back-projected by using a filter function having poor high-frequency response, thereby reconstructing the image with a small artifact.

Figure 16:
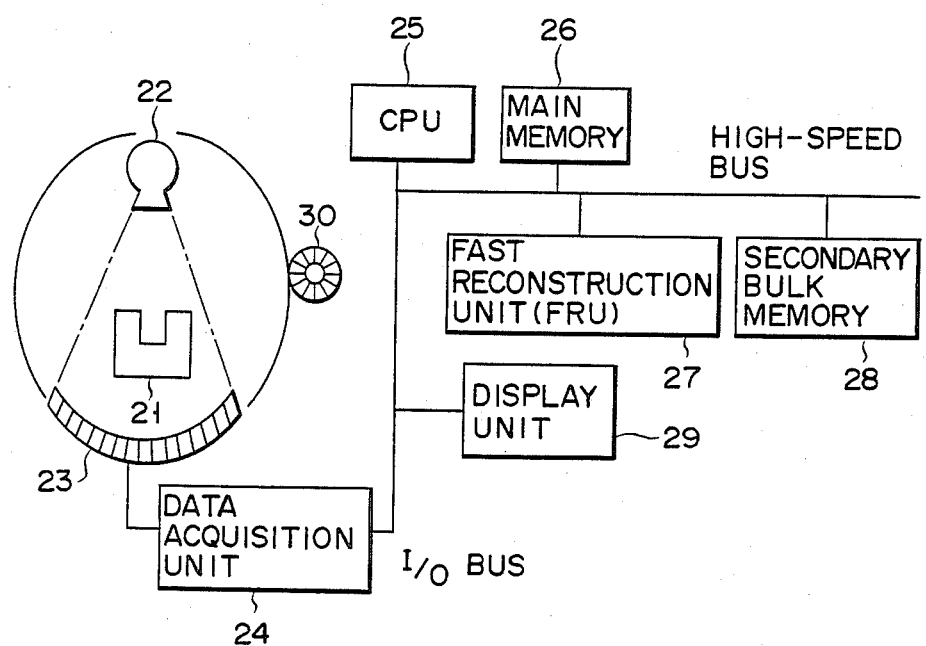

The above embodiment will be described with reference to the accompanying drawings. FIG. 16 is a schematic block diagram of a 3rd generation computerized tomography system. An X-ray as a fan beam having a radiation area covering an object 21 to be examined is emitted from an X-ray tube 22. A radiation sensor 23 is located opposite to the tube 22. The sensor 23 has sensor elements of a plurality of channels aligned in line of a fan beam expansion direction. The tube 22 and the sensor 23 are fixed and are located opposite to each other. The tube 22 and the sensor 23 are rotated about the object 21 while the tube 22 is located opposite to the sensor 23. The X-ray absorption data along different directions for a predetermined slice of the object can be acquired. For example, when the tube 22 and the sensor 23 are rotated through every 0.6 degrees, 300 projection data can be acquired. A detection current corresponding to an intensity of the incident radiation is integrated by a data acquisition unit 24 for every X-ray projection. The integrated analog data is A/D converted to obtain X-ray projection data. The overall system control is performed by a central processing unit (CPU) 25. The CPU 25 fetches data from the unit 24 and causes a main memory 26 to store the data. The CPU 25 also supplies an instruction and data to a high-speed reconstruction unit 27 which then convolutes the data and back-projects the convoluted data so as to reconstruct the image. The memory 26 has control program memory and operation execution areas for the CPU 25 and a memory area for temporarily storing X-ray absorption data derived from the unit 24. In this manner, the memory 26 serves as the main memory. Reference numeral 28 denotes a secondary bulk memory; and 29, a display unit for displaying a reconstructed image.

The memory 28 stores the images reconstructed by the unit 27 and X-ray absorption data. The unit 29 has a display section for displaying the image reconstructed by the unit 27 and a control section for controlling the system.

An X-ray emitted from the tube 22 is transmitted through the object 21 and reaches the sensor 23. During this period, a driver 30 is operated in synchronism with X-ray emission, and a table (not shown) for fixing and supporting the tube 22 and the sensor 23 is rotated. The tube 22 and the sensor 23 are rotated around the object 21, so that a large number of X-ray projections along different directions for a slice of the object 21 are performed.

The X-rays transmitted through the object along each projection direction are detected by the sensor 21. The detected analog signal is A/D converted by the unit 24 to a digital signal. The digital signal is supplied to the CPU 25. The CPU 25 causes the memory 28 to store the transmitted data and transmits it to the unit 27. The unit 27 performs predetermined preprocessing and filtering of the transmitted data. The filtered data is back-projected, and the image is thus reconstructed. The reconstructed image is supplied to the memory 28 and stored therein and to the unit 29. The unit 29 displays the reconstructed image.

Figure 17:
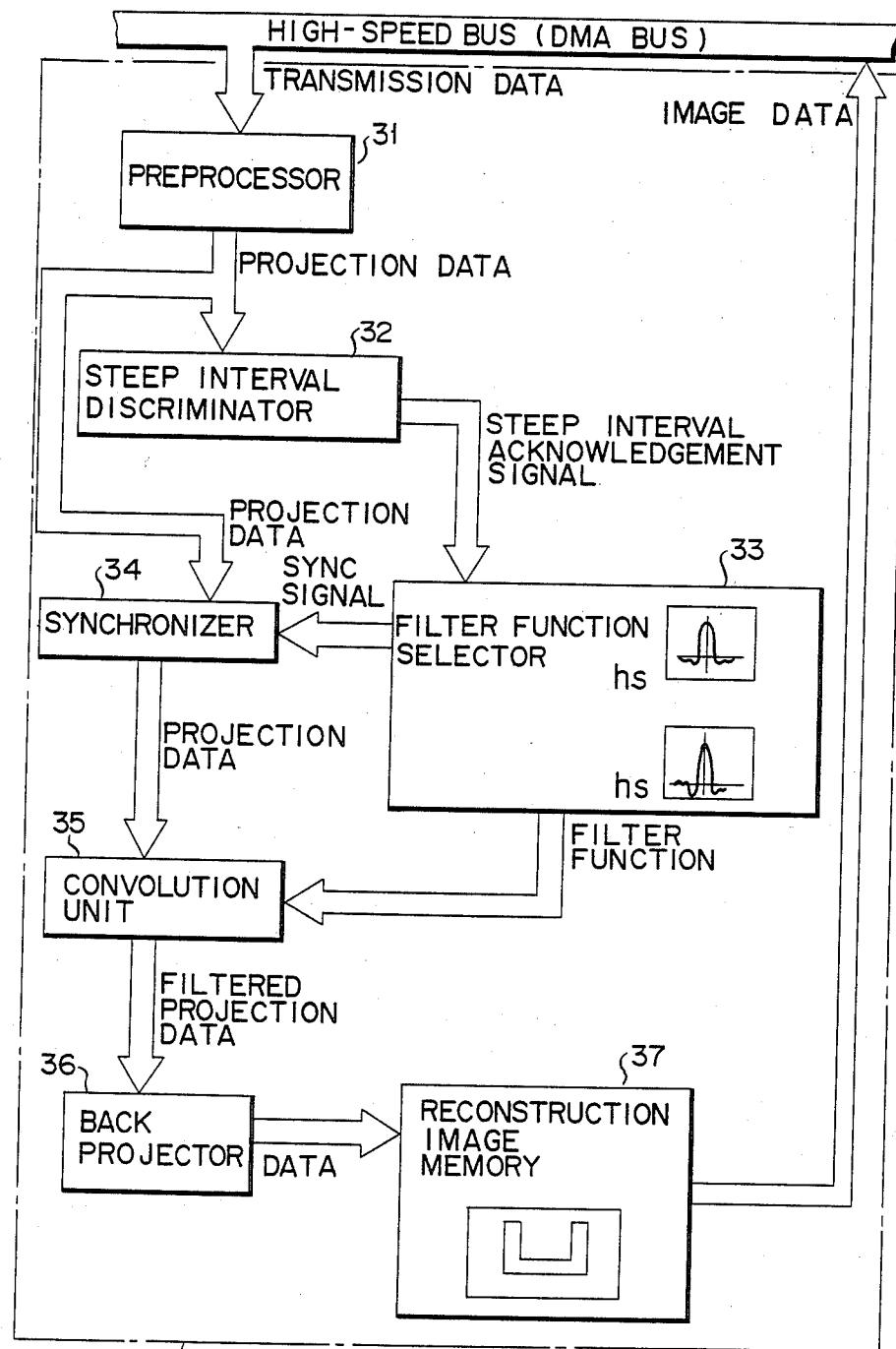

The unit 27 including a artifact elimination function will be described with referece to FIG. 17. A preprocessor 31 receives the transmitted data from the unit 24 through the CPU 25 and performs a correction (e.g., a beam hardening correction and a reference correction) and log transform. The preprocessed data is supplied to a steep interval discriminator 32 which detects an interval (i.e., the steep interval) during which data is rapidly changed. A steep interval acknowledge signal from the discriminator 32 is supplied to a filter function selector 33. The selector 33 selects a filter function having normal frequency responses or a filter function having poor high-frequency responses in response to the steep interval acknowledgement signal. The input timing of the projection data is controlled by a synchronizer 34. The data processed by the preprocessor 31 is saved by a convolution unit 35. The unit 35 convolutes the preprocessed data in accordance with the filter funtion selected by the selector 33. The convoluted data is supplied to a back projector 36. In this case, a plurality of filter functions may be stored, and one of them may be selected by the selector 33.

The projector 36 back-projects the data into a reconstruction image memory 37 in the projection angle direction, thereby reconstructing the image.

Figure 18:
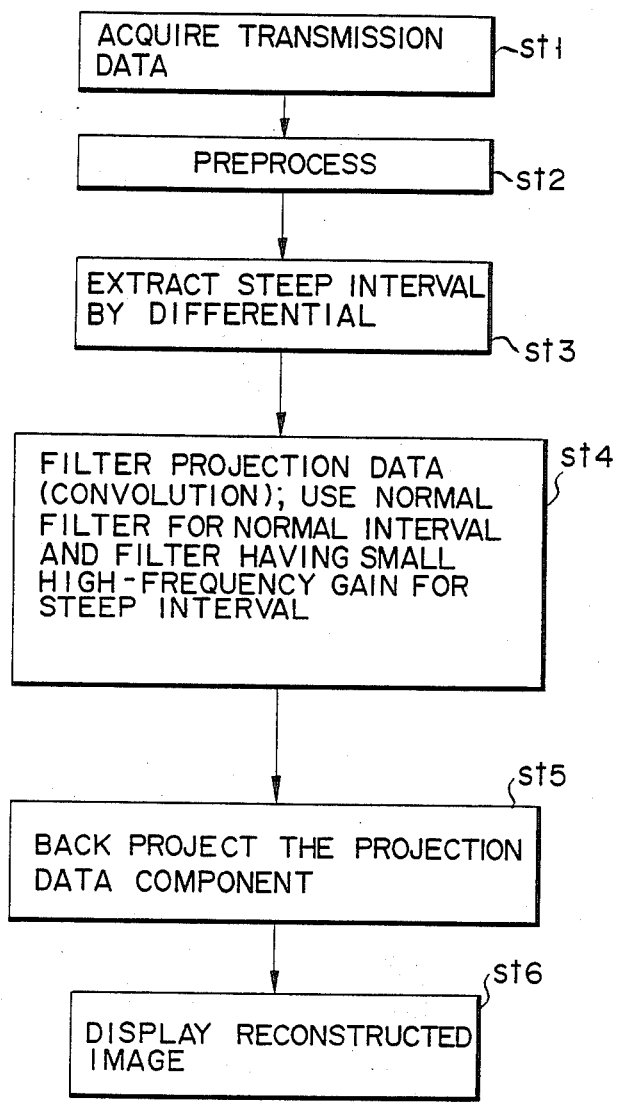

The operation of the apparatus having the arrangement described above will be described with reference to a flow chart of FIG. 18. When the transmitted data is acquired in step 1, preprocessing is performed in step 2. During preprocessing, a correction such as an offset correction and a reference correction, and log transform of the transmitted data P(x) are sequentially performed to prepare the projection data f(x). FIG. 19 is a graph showing the projection data f(x).

The projection data f(x) is supplied to the synchronizer 34 and the discriminator 32. In step 3, the discriminator 32 extracts steep intervals A, B, C and D of FIG. 19 from the projection data f(x). The projection data f(x) is divided into steep and moderate intervals. Data of the steep intervals A, B, C and D are supplied to the selector 33. In step 4, the selector 33 supplies a sync signal to the synchronizer 34 and selects a proper filter function which is supplied to the unit 35. In this case, during the steep interval of the convolution data, a filter function having poor high-frequency responses as shown in FIG. 20 is used. Otherwise, the normal filter function as shown in FIG. 21 is selected. The selected filter function is supplied to the unit 35.

The synchronizer 34 supplies the projection data to the unit 35 in response to the sync signal. The synchronizer 34 is not strictly a sync circuit but a kind of delay circuit for holding the data until the discriminator 32 determines the steep interval and the selector 33 selects the corresponding filter function. The unit 35 convolutes the projection data f(x) in accordance with the selected filter function h(x) in step 4. The convoluted data is supplied to the projector 36. The projector 36 back-projects the convoluted data to the memory 37 in step 5. When projections for all directions are completed, the image is transferred to another unit through a DMA bus. In step 6, a reconstructed image is displayed on the display unit.

Figure 22:
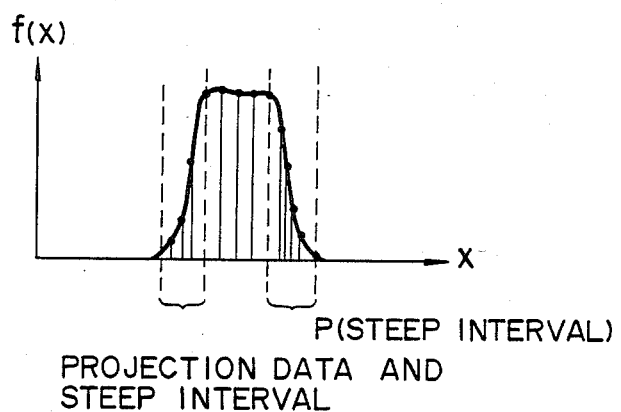
Figure 23:
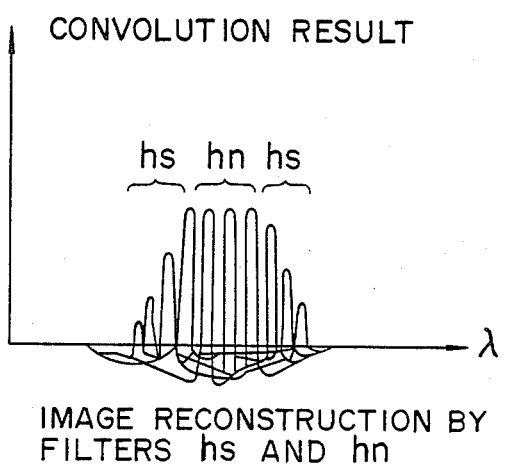

The selector 33 selects the filter function having the normal frequency responses and supplies it to the unit 35 during the interval excluding the steep interval. As shown in FIG. 22, the steep interval is deemphasized, while the normally filtered data is obtained during the normal interval. These data are convoluted, and an image is reconstructed, as shown in FIG. 23. For this reason, the steep interval causing the artifact is deemphasized, and a reconstructed image with little of artifact can be provided.

Figure 24:
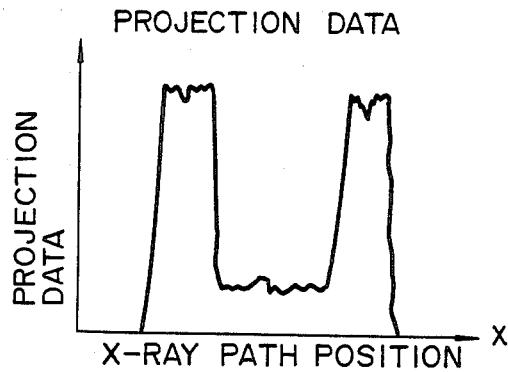
Figure 25:
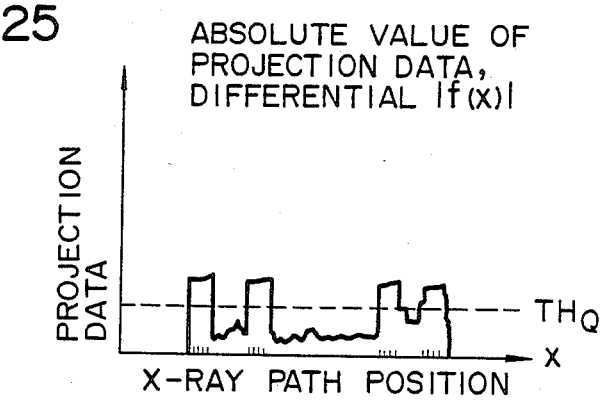
Figure 26:
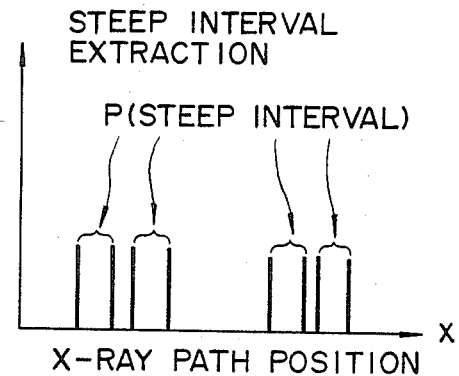

The steep interval discriminator 32 as the main part of this embodiment will be described in detail. The steep interval of the data can be extracted by general differential or sequential discrimination. When the differential is employed, the projection data is differentiated, as shown in FIG. 24, and the absolute values of the differentials of the projection data are obtained, as shown in FIG. 25. When Q (MIN steep interval) consecutive absolute values exceed a threshold value THQ, the continuous interval is detected as the steep interval, as shown in FIG. 26. For example, if Q=3 and THQ=64 (wherein the data length is given as 15 bits), and the steep interval comprises a continuous interval which exceeds the threshold value and two points respectively added to the two ends of the continuous interval.

Figure 27:
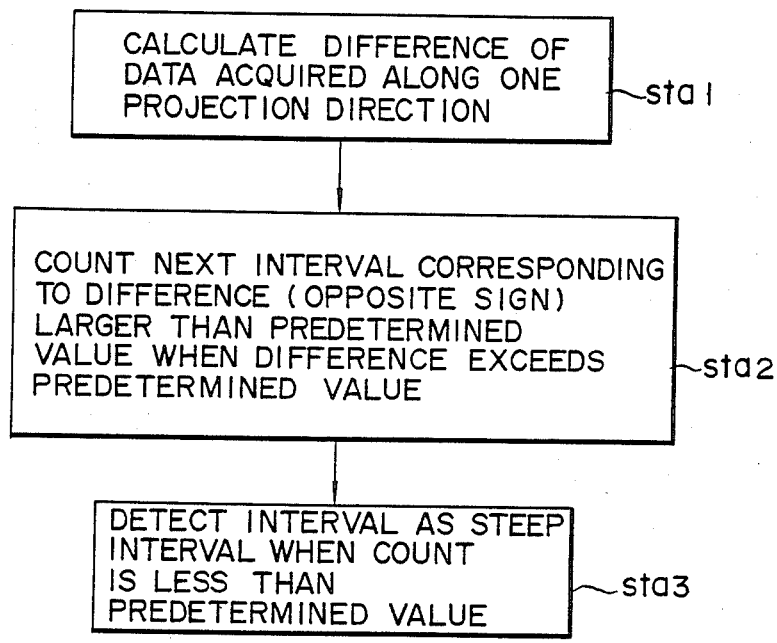

The differential type discriminator 32 is given as functional blocks in FIG. 27. In step 1, a difference of projection data (or every other projection data) along one projection direction is calculated. When the difference exceeds a predetermined value in step 1, an interval after which the sign of the difference is inverted is counted. In other words, the number of data during this interval is counted. In step 3, when the count is less than a predetermined value, the given interval is detected as a steep interval.

When sequential discrimination is performed, the respective values of the projections data strings are sequentially compared with the threshold value THQ to determine whether or not the data values are larger than the threshold value (steps 1 to 4), as shown in FIG. 28. If YES in step 3, the program runs to check whether or not an interval during which each difference is larger than the threshold value THQ continues to be longer than Q points (step 5 and 6).

If YES in step 6, an absolute value of a difference between the current data and the immediately preceding data is calculated and it is checked whether the difference is larger than the threshold value or not (steps 7 and 8). When the difference is smaller than the threshold value, the flow advances to step 9 to determine the steep interval. The flow returns to step 2 to search the next steep interval.

Figure 29:
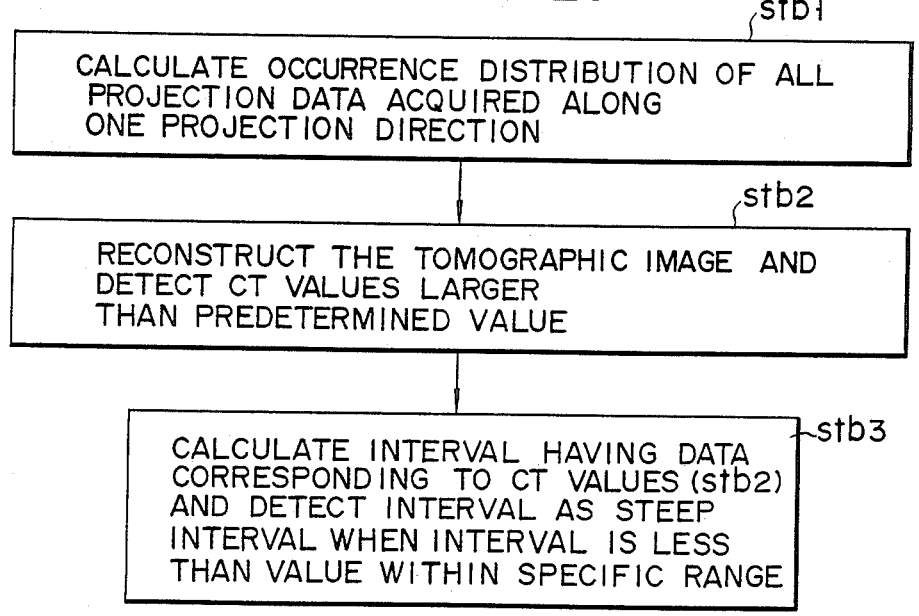

In this manner, the difference between two adjacent data values is checked. When the difference is larger than the predetermined value, the position where the difference becomes smaller than the predetermined value is checked to detect the steep interval. This is represented by the functional block diagram of FIG. 29.

The occurrence distribution of the projection data along the projection direction is obtained in step 1. In step 2, a CT value larger than a predetermined value is detected. In step 3, a given interval during which the data corresponds to the CT value is calculated. When the calculated interval is lower than the specific range, the given interval is detected as a steep interval.

Figure 30:
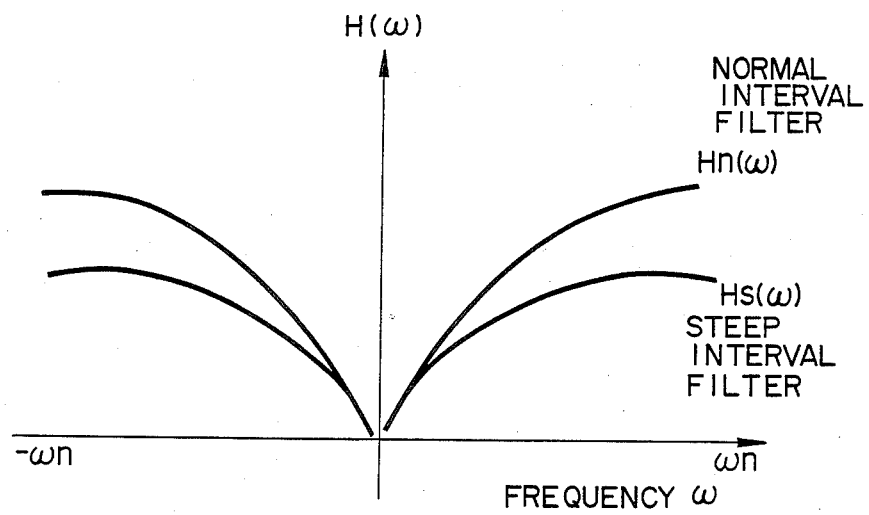

Finally, the filter function selector 33 and the filter functions will be described. As previously described, the filter function for the steep interval has poor high-frequency responses. FIG. 30 shows a filter function Hn(ω) having normal frequency responses and a filter function Hs(ω) having poor high-frequency responses and used in the steep interval.

The filter function Hn(ω) is like the Sheppu-Logan's function.

Two types of filter functions are prepared and selectively supplied to the unit 35.

Figure 31:
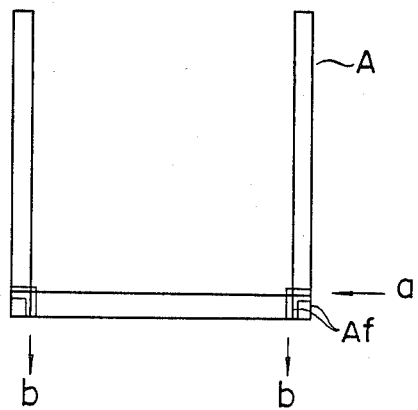
FIG. 31 is a sectional plan of a cup.

When reconstructing of the longitudinal cross-section of, for example, a cup A as shown in FIG. 31, then an artifact Af is liable to emerge at an intersection of the bottom surface with the side wall of the cup A. The reason for this is that the features of the image prominently emerge in the cases where the projection data a, b are acquired in a direction parallel to the side wall of the cup in comparison with the case where projection data are acquired under the other conditions.

According to the present invention, an interval during which the object properties typically appear is deemphasized, and image reconstruction is performed. For this reason, a distinct portion of the shape of the object can be sufficiently reconstructed without the corresponding projection data. When projection data representing a distinct portion is used without modification, an artifact often occurs. However, according to the present invention, this projection data is deemphasized to obtain a high-quality reconstructed image with little of artifact.

The present invention is not limited to computerized tomography using X-rays, but can be extended to other computerized tomography using other radiation sources as a radioisotope.

What is claimed is:

1. A computerized tomographic apparatus for reconstructing a slice of an object, comprising:
   means for projecting radiation on a slice of an object to be examined along each projection direction;
   means for detecting the radiation projected by said projecting means with a spatial resolution and generating radiation projection data along each projection direction; and
   means for reconstructing an image by using projection data generated from said projection data generating means and producing a reconstructed image corresponding to a radiation absorption coefficient at each position of said slice,
   said reconstructed image producing means comprising:
   means for dividing the projection data by at least one threshold value in accordance with an amplitude of said projection data;
   filter function means for storing and/or calculating different types of filter functions having frequency characteristics in accordance with the data characteristics; and
   means for convoluting the divided projection data in accordance with the filter functions corresponding to the data characteristics and back-projecting convoluted projection data,
   whereby the convoluted data having good high-frequency responses are obtained for the projection data having a higher degree of reliability, and are back-projected to obtain the reconstructed image.

2. An apparatus according to claim 1, wherein said reconstructed image producing means performs filtering in a real region.

3. An apparatus according to claim 1, wherein said reconstructed image producing means performs filtering in a frequency region.

4. A computerized tomographic apparatus for reconstructing a slice of an object comprising:
   means for projecting radiation on a slice of an object to be examined along each projection direction;
   means for detecting the radiation projected by said projecting means with a spatial resolution and generating radiation projection data along each projection direction; and
   means for reconstructing an image by using the projection data generated from said projection data generating means and producing a reconstructed image corresponding to a radiation absorption coefficient at each position of said slice,
   said reconstructed image producing means comprising:
   means for dividing the projection data by threshold values in accordance with the data characteristics:
   filter function means for storing and/or calculating different types of filter functions having frequency characteristics in accordance with the data characteristics; and
   means for convoluting the divided projection data in accordance with the filter functions corresponding to the data characteristics and back-projecting convoluted projection data,
   whereby the convoluted data having good high-frequency responses are obtained for the projection data having a higher degree of reliability, and are back-projected to obtain the reconstructed image;
   wherein said reconstructed image producing means divides the projection data in accordance with additional division.

5. A computerized tomographic apparatus for reconstructing a slice of an object comprising:
   means for projecting radiation on a slice of an object to be examined along each projection direction;
   means for detecting the radiation projected by said projecting means with a spatial resolution and generating radiation projection data along each projection direction; and
   means for reconstructing an image by using the projection data generated from said projection data generating means and producing a reconstructed image corresponding to a radiation absorption coefficient at each position of said slice,
   said reconstructed image producing means comprising:
   means for dividing the projection data by threshold values in accordance with the data characteristics:
   filter function means for storing and/or calculating different types of filter functions having frequency characteristics in accordance with the data characteristics; and
   means for convoluting the divided projection data in accordance with the filter functions corresponding to the data characteristics and back-projecting convoluted projection data,
   whereby the convoluted data having good high-frequency responses are obtained for the projection data having a higher degree of reliability, and are back-projected to obtain the reconstructed image;
   wherein said reconstructed image producing means divides the projection data in accordance with proportional additional division.

6. A computerized tomographic apparatus for reconstructing a slice of an object comprising:
   means for projecting radiation on a slice of an object to be examined along each projection direction;
   means for detecting the radiation projected by said projecting means with a spatial resolution and generating radiation projection data along each projection direction; and
   means for reconstructing an image by using the projection data generated from said projection data generating means and producing a reconstructed image corresponding to a radiation absorption coefficient at each position of said slice,
   said reconstructed image producing means comprising:
   means for dividing the projection data by threshold values in accordance with the data characteristics;
   filter function means for storing and/or calculating different types of filter functions having frequency characteristics in accordance with the data characteristics; and
   means for convoluting the divided projection data in accordance with the filter functions corresponding to the data characteristics and back-projecting convoluted projection data, whereby the convoluted data having good high-frequency responses are obtained for the projection data having a higher degree of reliability, and are back-projected to obtain the reconstructed image;

wherein said reconstructed image producing means comprises:

means for calculating threshold values for dividing projection data into a predetermined number of regions;

means for calculating filter functions having frequency characteristics corresponding to said regions divided by the threshold values; and means for convoluting the projection data of each projection direction by the filter function corresponding to each region and for obtaining data for back projection, whereby the convoluted data having good high-frequency characteristics are obtained for the projection data having a higher degree of reliability, and are back-projected to obtain the reconstructed image.

7. An apparatus according to claim 6, wherein said reconstructed image producing means performs filtering by dividing the projection data of each projection into the regions.

8. An apparatus according to claim 6, wherein said reconstructed image producing means analyzes the projection data of each projection to obtain a standard filter function and performs division filtering of the projection data of all projections with the standard filter function.

9. An apparatus according to claim 6, wherein the regions for filtering by said reconstructed image producing means are obtained such that a maximum or minimum value of the projection data is calculated, a range between the maximum or minimum value and a standard level is calculated, and the range is equally divided into the predetermined number of regions.

10. An apparatus according to claim 6, wherein the regions for filtering by said reconstructed image producing means are obtained by dividing the projection data in accordance with a change in distribution thereof.

11. An apparatus according to claim 6, wherein the filter function corresponding to each region subjected to filtering by said reconstructed image producing means is calculated in accordance with a specific value within the region.

12. An apparatus according to claim 6, wherein the filter function corresponding to each region subjected to filtering by said reconstructed image producing means is selected from empirically derived filter functions in accordance with a specific value within the region.

13. A computerized tomographic apparatus for reconstructing a slice of an object comprising:

means for projecting radiation on a slice of an object to be examined along each projection direction;

means for detecting the radiation projected by said projecting means with a spatial resolution and generating radiation projection data along each projection direction; and means for reconstructing an image by using the projection data generated by said projection data generating means and producing a reconstructed image corresponding to a radiation absorption coefficient at each position of said slice, said reconstructed image producing means comprising:

means for dividing the projection data in accordance with degree of steepness of a change in the projection data; and means for selecting a filter function corresponding to each divided projection data, whereby the projection data is convoluted by using the corresponding filter functions, and convoluted projection data is back-projected to reconstruct an image for said slice.

14. An apparatus according to claim 13, wherein a filter having poor high-frequency emphasis characteristics is used during a steep interval, and a normal filter function is used in an interval excluding the steep interval, thereby convoluting the projection data.

* * * * *